United States Patent [19]

Grobe

[11] Patent Number: 5,112,310
[45] Date of Patent: May 12, 1992

[54] APPARATUS AND METHODS FOR PERCUTANEOUS ENDOSCOPIC GASTROSTOMY

[76] Inventor: James L. Grobe, 550 S. Beretania St., Honolulu, Hi. 96813

[21] Appl. No.: 651,558

[22] Filed: Feb. 6, 1991

[51] Int. Cl.⁵ .................. A61M 25/00; A61M 5/00
[52] U.S. Cl. .................. 604/175; 604/49; 604/96; 604/105; 604/164
[58] Field of Search ............ 604/175, 173, 164, 105, 604/106, 27, 49, 48, 96

[56] References Cited

U.S. PATENT DOCUMENTS

| | | | |
|---|---|---|---|
| 3,397,699 | 8/1968 | Kohl | 604/105 |
| 3,640,281 | 2/1973 | Robertson | 604/264 |
| 4,315,513 | 2/1982 | Nawash et al. | 128/348 |
| 4,666,433 | 5/1987 | Parks | 604/178 |
| 4,668,225 | 5/1987 | Russo et al. | 604/270 |
| 4,676,782 | 6/1987 | Yamamoto et al. | 604/175 |
| 4,758,219 | 7/1988 | Sacks et al. | 604/54 |
| 4,762,519 | 8/1988 | Frimberger | 604/280 |
| 4,767,404 | 8/1988 | Renton | 604/48 |
| 4,769,014 | 9/1988 | Russo | 604/270 |
| 4,775,362 | 10/1988 | Kronner | 604/96 |
| 4,781,682 | 11/1988 | Patel | 604/105 |
| 4,781,694 | 11/1988 | Branemark et al. | 604/175 |
| 4,781,704 | 11/1988 | Potter | 604/105 |
| 4,795,430 | 1/1989 | Quinn et al. | 604/97 |
| 4,826,481 | 5/1989 | Sacks et al. | 604/54 |
| 4,861,334 | 8/1989 | Nawaz | 604/49 |
| 4,863,438 | 9/1989 | Gauderer et al. | 604/247 |
| 4,900,306 | 2/1990 | Quinn et al. | 604/97 |
| 4,921,479 | 5/1990 | Grayzel | 604/53 |
| 4,944,732 | 7/1990 | Russo | 604/247 |
| 5,019,032 | 5/1991 | Robertson | 604/49 |

OTHER PUBLICATIONS

"Percutaneous Endoscoptic Gastrostomy: Indications, Limitations . . . ," Ponsky et al., vol. 13, No. 2, World Journal of Surgery, 1989.
"Percutaneous Endoscopic Gastrostomy," Mamel, The American Journal of Gastrostomy, vol. 84, No. 7, pp. 703-710.
"Introducing Flexiflow Stomate Low Profile Gastrostomy Kit" brochure, Ross Laboratories, Mar. 1989.
"The New Superior GastroPort—Long Term Enteral Feeding Made Easier!" brochure, Lafayette Pharmaceuticals, Inc., 1987.
"In Gastroescophageal Reflux Disease—Raising the Head is not Enough" brochure, Bard Interventional Products, 1988.
"Friction-Lock Malecot Russell Gastostomy Set and Tray" brochure, Cook Incorporated, 1986.
"A New Dawn of Technology for Tomorrow's Health Care" brochure, Applied Medical Technology.
"Enteral Feeding Products" brochure, Ross Laboratories, Jul. 1987.
"Flexiflow Introducer Gastrostomy Kit" brochure, Ross Laboratories, Mar. 1990.

*Primary Examiner*—Paul J. Hirsch
*Attorney, Agent, or Firm*—Nixon & Vanderhye

[57] ABSTRACT

The gastrostomy tube includes an elongated flexible wire guide and an elongated sleeve having a tapered end portion, the guide and sleeve having lengths sufficient to extend from a location outside the abdominal wall of the patient through the patient's stomach and esophagus and out the patient's mouth. The gastrostomy tube has a retention device in the form of an inflatable balloon or expandable and retractable cage adjacent an end portion for retaining the tube within the patient's stomach. In use, a guide wire is introduced through an incision through the abdominal and gastric walls under endoscopic observation and pulled out the patient's mouth. The sleeve, tapered end first, is passed along the wire through the patient's mouth, esophagus and stomach, and out through the incision. After the guide wire is withdrawn from the sleeve, the gastrostomy tube is inserted over the sleeve, its feeding end located within the stomach, and the retention device is activated to retain the gastrostomy tube within the stomach.

21 Claims, 8 Drawing Sheets

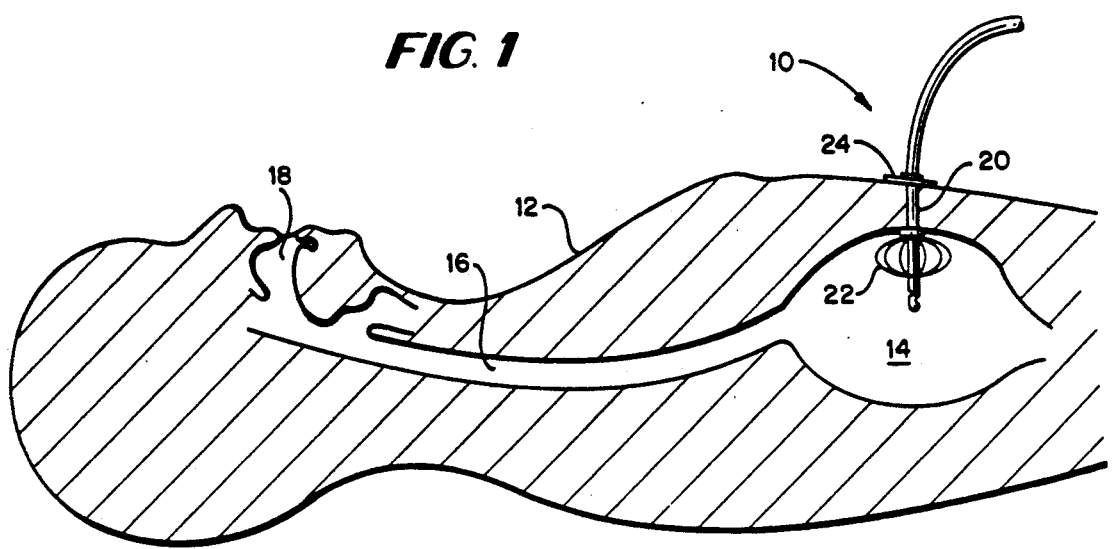
FIG. 1
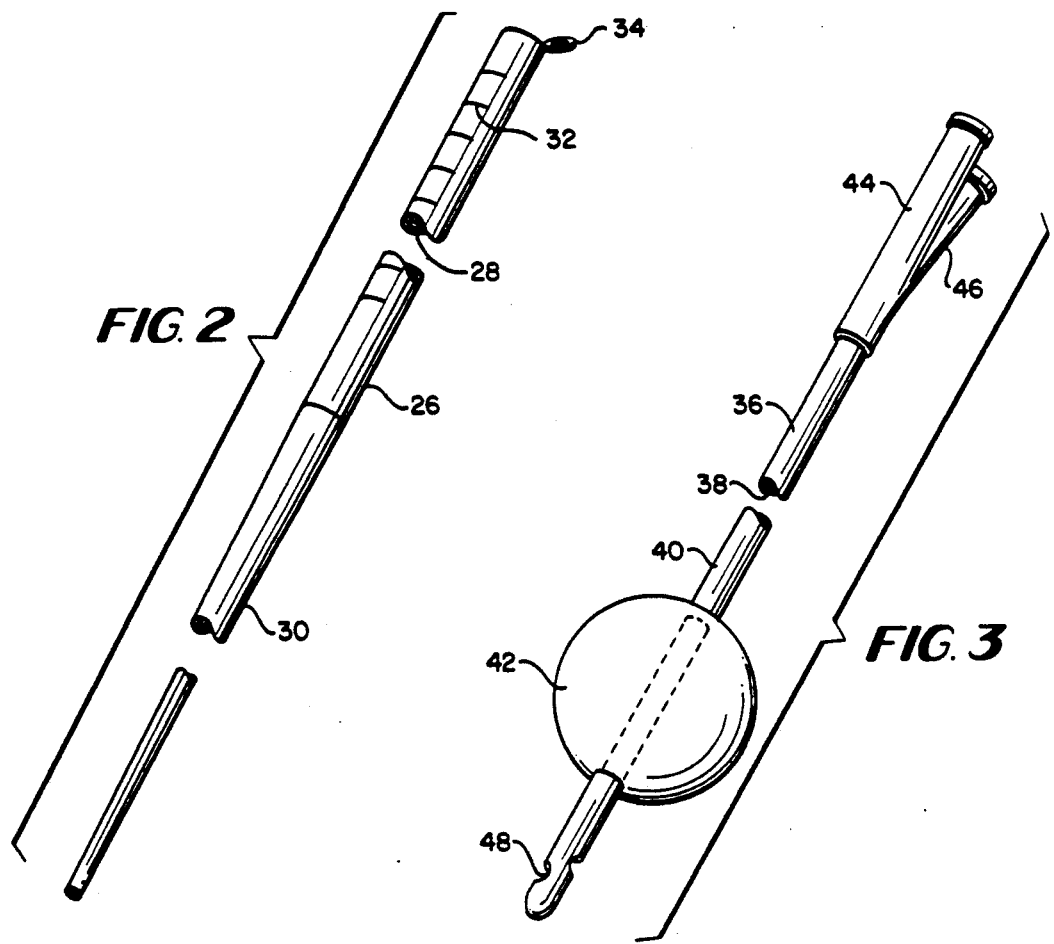
FIG. 2
FIG. 3

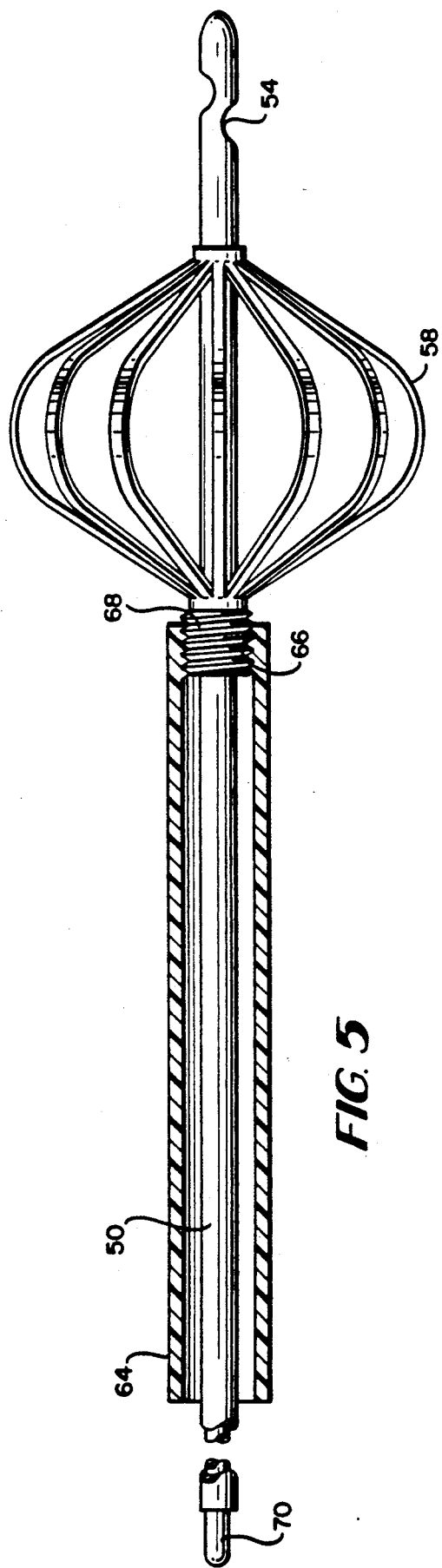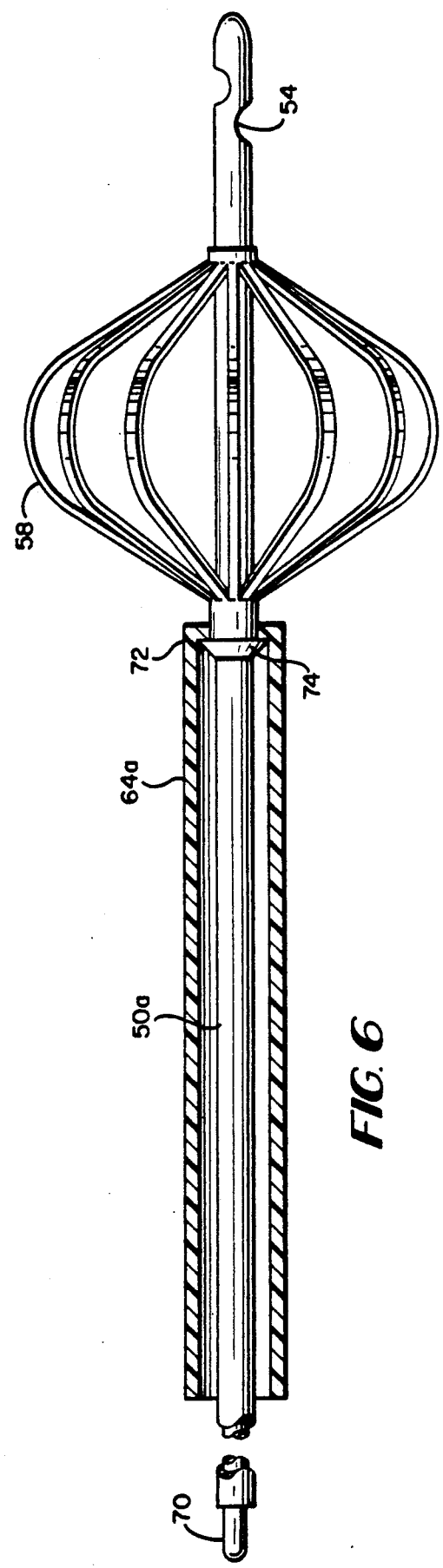

APPARATUS AND METHODS FOR PERCUTANEOUS ENDOSCOPIC GASTROSTOMY

BACKGROUND OF THE INVENTION

The present invention relates to novel and improved apparatus and methods for percutaneous endoscopic gastrostomy. Particularly, the present invention relates to a kit containing various devices used in the gastrostomy apparatus and technique hereof, to the devices per se and to the technique itself.

Percutaneous endoscopic gastrostomy (PEG) was recently introduced as an alternative to surgically created feeding gastrostomy for nutritional support for the ill. The purpose of both techniques is to provide long-term tube access in those individuals unable to take oral nutrition, particularly for feeding directly across the abdominal and gastric walls into the stomach. Despite its relatively recent introduction, PEG has gained wide acceptance as a safe, time-tested and well-recognized method which avoids general anesthesia and laparotomy, allows earlier use of the feeding tube and reduces overall costs.

Currently, there are three variations of the PEG technique, known generally as the "Pull," "Push," and "Introducer" techniques. In all of these methods, as well as the method of the present invention, the patient is similarly prepared. For example, the patient is fasted for at least eight hours, prophylactic antibiotics are given and, with the patient in the supine position, the abdomen is prepared and local sedation is given. These preparatory procedures are conventional and need not be described in detail. In the "Pull" method, an endoscope is inserted into the patient's mouth and passed through the esophagus into the stomach. After distension of the stomach by inflation, the incision site is identified and an incision is made. A cannula, with an outer sheath, is inserted through the incision across the abdominal and gastric walls and into the snare loop on the endoscope end within the stomach. By grasping the cannula, the needle may be removed and a suture is passed through the cannula into the stomach. The endoscopic snare then grasps the suture, the cannula is released, and the endoscope and suture are withdrawn through the esophagus and mouth of the patient. A gastrostomy tube is then secured to the suture end and is pulled retrograde into the esophagus and stomach, emerging through the abdominal wall. When the head or retention device on the gastrostomy tube engages the gastric wall under observation by the reinserted endoscope, an outer retention device is applied to the gastrostomy tube to hold the gastric and abdominal walls in close contact. After a sufficient waiting period, the patient may then be fed through the gastrostomy tube.

In the "Push" technique, the patient is similarly prepared and the incision is made. However, instead of a suture, a flexible wire is passed through the cannula. The endoscopic snare grasps the wire and the endoscope and wire are pulled out the patient's mouth. The gastrostomy tube is then applied to and about the wire with its tapered end first. The guide wire is held taut as the gastrostomy tube is pushed over the guide wire, through the patient's mouth and esophagus, into the stomach and out the abdominal wall. When the retention device on the end of the gastrostomy tube is correctly positioned under endoscopic observation, the guide wire is removed and the outer retention device applied, whereby the patient may be fed in due course.

In the "Introducer" technique, a needle is inserted into the stomach through the incision and a guide wire is passed through the needle lumen. After the needle is removed, an "Introducer" with a peel-away sheath is passed over the guide wire into the stomach. The "Introducer" is then removed and a catheter is inserted through the sheath, the catheter having a Foley balloon at its end which is then inflated to retain the catheter in place. The sheath is then peeled away, leaving only the catheter in the stomach. After the outer retention device is applied, the patient may be fed in due course.

In accordance with the present invention, there is provided apparatus, for example, in the form of a "PEG" kit, and a technique for PEG which, as explained below, has various advantages over and addresses several of the shortcomings of each of the previously described "Pull," "Push" and "Introducer" PEG techniques. In the present invention, the apparatus essentially comprises a sleeve tube and a gastrostomy tube specifically adapted for use with one another and with other devices and implements which are currently used for the above-described conventional techniques. The sleeve comprises a tubing, preferably formed of plastic, having a thickness sufficient only to maintain substantial rigidity, while simultaneously being bendable and deformable. The interior diameter of the tube is sufficient to accommodate a gastrostomy feeding tube. The sleeve tube also has a length sufficient such that one end may exit the skin at the abdominal wall, while the other end remains outside the patient's mouth as the tube is being inserted. Additionally, the tube has a tapered end portion which gradually increases in diameter over approximately one-half of the length of the tube. The tube is provided adjacent the end opposite the tapered portion. Graduations to facilitate positioning the tube in the patient are provided. Further, an internal stabilizing loop is secured at the tip of the tapered end portion of the tube. The loop may comprise a soft plastic or thread bonded to the tube, having an elongated shape, and disposed with some degree of rigidity at a slight angle to the tube to preclude obstruction of the passage of the gastrostomy tube through the sleeve tube opening.

The gastrostomy tube for use with the present invention is preferably formed of a plastic material and has a diameter for reception within the sleeve tube. The gastrostomy tube has an integral expandable and retractable retention device at one end to facilitate its securement within the gastric wall. Such retention device may comprise an inflatable balloon or an expandable and retractable basket. With a balloon retention device, the external portion of the gastrostomy tube has a Y-configuration, with one branch for feeding purposes and the other tube for inflation and deflation of the balloon. Where a balloon is used, the balloon should have a configuration when inflated to enable a large area of contact between the balloon and the gastric wall. Also, either air or water inflation may be used. In the basket-type retention device, the basket includes a plurality of circumferentially spaced ribs secured at one end adjacent the inner end of the gastrostomy tube. The opposite end of the ribs is secured to a collar slidable on the gastrostomy tube such that, depending upon the position of the collar along the tube, the ribs are expanded radially outwardly or deflated radially inwardly to lie substantially parallel to and in contact with the gastrostomy tube end.

The PEG apparatus hereof, preferably supplied in a kit form, may also include a guide wire, needle catheter with stylette, an external retention device and a retrieval tube. The guide wire, catheter with stylette and external retention device may be conventional in construction. However, the retrieval tube hereof is used to facilitate removal of the gastrostomy tube from the stomach. The retrieval tube is particularly useful with the gastrostomy tube having the basket retention device. The retrieval tube is preferably provided with an end adapter specifically configured for cooperation with the collar on the basket, depending on the type of connection desired therebetween. For example, the collar on the end of the retrieval tube may comprise a plurality of circumferentially spaced hooks for engaging complementary hooks formed on the collar. Alternatively, the retrieval tube may have a screw thread for threaded engagement with the threaded collar on the basket retention device. In either case, when the retrieval tube is passed over the gastrostomy tube and connected to the collar, relative motion between the retrieval tube and gastrostomy tube enables the basket ribs to flatten along the side of the gastrostomy tube whereby the latter may be withdrawn.

To use the afore-described apparatus, the patient is prepared similarly as previously described as with respect to the "Push," "Pull," and "Introducer" techniques. With the endoscope passed through the mouth and esophagus into the stomach of the patient and the incision site located, a needle with internal stylette is passed through the incision into the stomach. The stylette is removed and the flexible guide wire is passed through the needle into the stomach and grasped with the endoscopic snare. The guide wire is then pulled with the endoscope through the esophagus and out the patient's mouth. The sleeve is disposed on the guide wire, tapered end first, and advanced along the guide wire through the mouth and esophagus into the stomach and out through the abdominal wall. With the endoscope reinserted into the stomach, the tapered end of the sleeve is pulled out through the abdominal wall to dilate the tract and locate the non-tapered end within the stomach short of the incision. The endoscopic snare is used to grasp the inner end of the sleeve to stabilize the sleeve during the remainder of the procedure. The guide wire is then removed and the sleeve is cut a distance, for example, several centimeters, above the skin to remove the tapered segment of the sleeve.

A gastrostomy tube is inserted into the stomach through the sleeve under endoscopic observation. To facilitate insertion, the adjoining walls of the gastrostomy tube and the sleeve may be lubricated. Also, a removable stiffening wire or rod may be used in the gastrostomy tube to facilitate its passage through the sleeve. Once the end of the gastrostomy tube is located within the stomach, the internal retention device is inflated or expanded and fixed in position. The sleeve is now withdrawn over the gastrostomy tube and removed by known techniques. Alternatively, the sleeve could be left in place over the external portion of the gastrostomy tube and later removed at the time of the first replacement of the gastrostomy tube. An outer retention device is then applied to the gastrostomy tube and the gastrostomy tube is secured in place.

To remove the gastrostomy tube, the balloon or basket internal retention device is deflated or contracted by external manipulation of the gastrostomy tube. For example, the balloon may be vented. To contract the basket retention device, a retrieval tube may be disposed about the gastrostomy tube and connected by either a snap-fit or threaded fit with the collar on the basket. When connected, relative movement of the retrieval tube and the gastrostomy tube enables the basket ribs to lie flat against the gastrostomy tube and the latter to be withdrawn from the ostomy tract. Reinsertion of a gastrostomy tube after the ostomy tract has matured is accomplished by inserting the new gastrostomy tube through the ostomy tract with the internal retention devices flattened or deflated along the gastrostomy tube. Thereafter, when the inner end of the gastrostomy tube is properly located, the balloon is inflated or the basket is expanded to retain the tube in the mature ostomy tract.

Various advantages are obtained when using the technique of the present invention. By using the unique internally delivered dilating tapered sleeve to dilate the tract as the sleeve is passed from the inside of the stomach out through the abdomen, optimum direction of force is maintained during the dilation period. The pressure of the tube dilating the tract in this direction maintains the desired apposition of the stomach and abdominal walls rather than tending to separate those walls as in other techniques, for example, the "Introducer" technique described above. The external placement of the gastrostomy tube by use of the internally delivered dilating sheath enables both deployment and retraction of the internal retention device from the outside, subsequent to removal, and replacement of the gastrostomy tube without the need of endoscopy. In the "Pull" and "Push" techniques, removal of the initially disposed gastrostomy tube requires endoscopic removal of the internal retention device. This increases the overall cost of maintaining tube feeding but also exposes the patient to the risk of an additional procedure, as well as the risk of extraction of the internal retention device through the upper airway.

Additionally, because the internal retention device of the present invention does not have to traverse the mouth and esophagus to be positioned in the stomach, the present apparatus and technique is usable in a greater number of patients, i.e., those patients exhibiting narrowing in those areas than is currently possible with the "Push" and "Pull" techniques. Also, the basket-type retention device, with the screw-lock or snap-lock lessens the chance of inadvertent retraction and removal of the gastrostomy tube.

The present invention may also include a jejunostomy tube which is basically similar to the gastrostomy tube described above, except that it has a longer distal end for placement in the small bowel for feeding. The distal end is weighted to facilitate passage of the tube into the jejunum and maintain the position of the tube in the small bowel. Preferably, the jejunostomy tube has an internal stiffening wire to aid in tube tip placement. An alternate form of jejunostomy tube may be provided with a second internal tube, either concentrically or radially spaced from the feeding tube, wherein the second tube has ports or openings in the stomach allowing for simultaneous gastric suction for decompression of the stomach while providing small bowel feedings.

The method of insertion of the jejunostomy tube is similar to that for the gastrostomy tube as describe above to the point of expansion of the internal retention device. To facilitate proper placement of the jejunostomy tube, the distal tube tip is provided with a small thread loop. An endoscopic snare or forceps are used to grasp the thread loop, which is then advanced into the small bowel as far as possible. The thread loop is then released and the endoscope withdrawn. The stiffening wire is also removed. The withdrawal procedure for the jejunostomy tube is identical to that for the gastrostomy tube described above.

Preferably, the apparatus described above for percutaneous endoscopic gastrostomy is provided in kit form. The apparatus necessary for inclusion in the kit include the sleeve tube, needle cannula with stylette, guide wire, retrieval tube and stiffening rod (for basket-type retention), gastrostomy tube (basket or balloon-type) and an external retention device. One or more of the following items may be included in the kit as desired, an inflation syringe (for balloon-type), scalpel, local anesthetic, a syringe and needle for local anesthetic, gauze, sterile drape, cleansing solution and scissors. A jejunostomy tube insertion kit would include those essential items described above for the gastrostomy insertion kit, except that the jejunostomy tube would be included instead of the gastrostomy tube. The present invention also encompasses a replacement gastrostomy tube kit. This kit would include a gastrostomy tube and a retrieval tube and stiffener (basket-type). If a balloon-type retention device is used, an inflation syringe would be included in the kit in lieu of the stiffener useful for the basket-type retention device. Additionally, a replacement jejunostomy tube kit may be provided similarly as described above with respect to the replacement gastrostomy tube kit. In the jejunostomy tube kit, however, the kit would include the jejunostomy tube in lieu of the gastrostomy tube.

In a preferred embodiment according to the present invention, there is provided a procedure for percutaneous endoscopic gastrostomy using a guide wire, a sleeve having a tapered end and a gastrostomy tube having a retention device adjacent one end, comprising the steps of (a) passing an endoscope through a patient's mouth and esophagus and into the patient's stomach, (b) introducing the guide wire through the patient's abdominal and gastric walls and into the patient's stomach, (c) grasping a portion of the guide wire within the stomach, (d) pulling the endoscope and guide wire from the stomach out the patient's mouth, (e) passing the sleeve, tapered end first, over the wire through the patient's mouth, esophagus and stomach and out through the abdominal and gastric walls, leaving terminal portions of the sleeve on opposite sides of the abdominal and gastric walls, (f) withdrawing the guide wire from the sleeve, (g) inserting the gastrostomy tube through the sleeve to locate the end thereof carrying the retention device within the stomach and (h) activating the retention device to retain the gastrostomy tube within the stomach.

In a further preferred embodiment according to the present invention, there is provided apparatus for performing percutaneous endoscopic gastrostomy comprising an elongated flexible guide wire having a length sufficient to extend from a location outside the abdominal wall of a patient through the patient's stomach and esophagus and out the patient's mouth, an elongated sleeve having a tapered end portion and an internal diameter sized to enable slidable movement thereof along the guide wire, the sleeve having a length sufficient to extend from a location outside the abdominal wall of a patient through the patient's stomach and esophagus and out the patient's mouth and a gastrostomy tube for reception within the sleeve and having a retention device adjacent an end portion thereof for retaining the gastrostomy tube within the patient's stomach in position for feeding.

In a further preferred embodiment according to the present invention, there is provided a percutaneous endoscopic kit comprising a container, a needle cannula with stylette in the container, and an elongated flexible guide wire in the container. The wire has a length sufficient to extend from a location outside the abdominal wall of a patient through the patient's stomach and esophagus and out the patient's mouth. Also provided is an elongated sleeve in the container, having a tapered end portion and an internal diameter sized to enable slidable movement thereof along the guide wire, the sleeve having a length sufficient to extend from a location outside the abdominal wall of a patient through the patient's stomach and esophagus and out the patient's mouth. One of a gastrostomy tube or jejunostomy tube for reception within the sleeve and a retention device for location adjacent an end portion of one tube for retaining one tube in position for feeding are also provided in the container.

Accordingly, it is a primary object of the present invention to provide novel and improved apparatus and methods for percutaneous endoscopic gastrostomy having various advantages in concept, construction, mode of use and result in comparison with prior percutaneous endoscopic gastrostomy apparatus and techniques.

These and further objects and advantages of the present invention will become more apparent upon reference to the following specification, appended claims and drawings.

BRIEF DESCRIPTION OF THE DRAWING FIGURES

FIG. 1 is a schematic cross-sectional view of the upper torso of a human illustrating a gastrostomy device according to the present invention in place;

FIG. 2 is a perspective view with parts broken out and in cross-section illustrating a sleeve for use with the gastrostomy device hereof;

FIG. 3 is a perspective view with parts broken out and in cross-section illustrating a gastrostomy tube employing an inflatable inner retention device;

FIG. 5 is a longitudinal cross-sectional view with parts broken out and in cross-section of the gastrostomy tube and retrieval tube illustrated in FIG. 4 with a threaded connection therebetween;

FIG. 6 is a view similar to FIG. 5 illustrating a different form of connection between the retrieval tube and retention device;

DETAILED DESCRIPTION OF THE DRAWING FIGURES

Figure 4A:
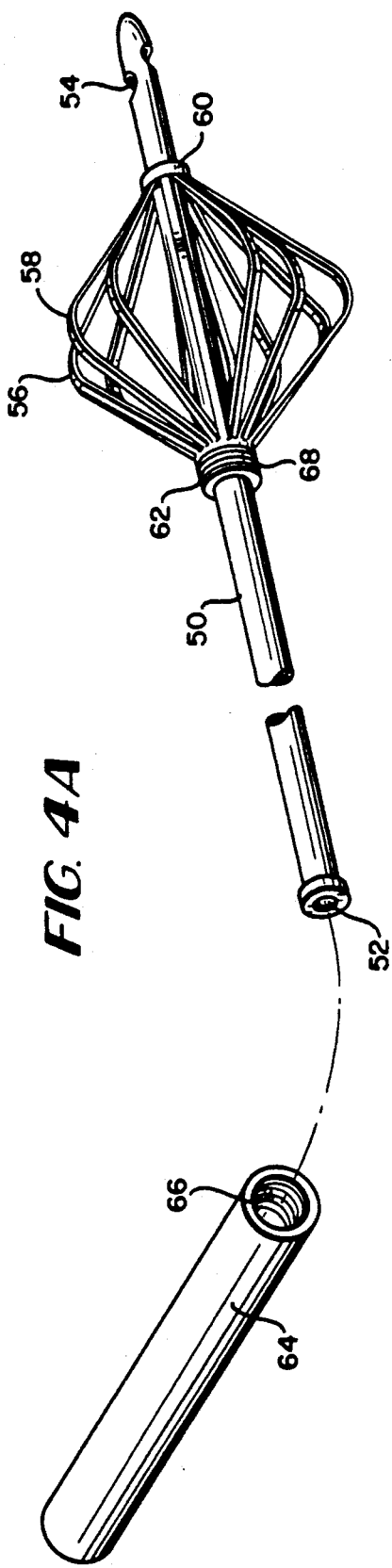
FIG. 4A is a perspective view with parts broken out and in cross-section illustrating a basket-type retention device at the end of a gastrostomy tube according to the present invention and further illustrating a retrieval tube.

Reference will now be made in detail to a present preferred embodiment of the invention, an example of which is illustrated in the accompanying drawings.

Referring now to the drawings, particularly to FIG. 1, there is illustrated a gastrostomy tube, generally designated 10, extending through the abdominal and gastric walls and providing a feeding tube for supplying nutritional needs to a patient 12 and directly into the patient's stomach 14. For reference herein, the patient's esophagus and mouth are designated 16 and 18, respectively. The gastrostomy tube 10 is representative of either of the two types illustrated herein, as well as others, and it will be seen that generally the gastrostomy tube 10 includes a feeding tube 20 disposed between inner and outer retention devices 22 and 24, respectively. The inner retention device 22 illustrated in FIG. 1 corresponds to the retention device illustrated in FIGS. 4, 5 and is used to illustrate the technique hereof in FIGS. 7A-7F. It will be appreciated that the inflatable type of gastrostomy tube illustrated in FIG. 3, as well as other types, may be employed in lieu of the gastrostomy tube specifically illustrated in FIG. 1.

Referring now to FIG. 2, the gastrostomy apparatus according to the present invention includes an elongated sleeve 26 formed of a material, such as plastic, which has some rigidity but is bendable and deformable. The outer diameter of the sleeve 26 may be approximately 16-24 fr. Sleeve 26 includes an inner passageway 28 opening through the opposite ends. The inner diameter is sufficiently large to accommodate a feeding tube with an outer diameter of between 14-20 fr. The sleeve 26 is formed of a length such that its opposite ends would extend from the patient's mouth 18, through the esophagus and to a location outside the abdominal wall at the ostomy site. The sleeve 26 is tapered along one end, as illustrated at 30. The taper extends for at least substantially one-half the length of the sleeve 26. Graduations 32 are provided along the end of the sleeve 26 opposite its tapered end for purposes of locating the sleeve 26 in use as described hereinafter. The graduations measure the distance from the end of the tube opposite its tapered end. At the same end, there is provided a stabilizing loop 34. The loop may be formed of a soft plastic material or a thread bonded to the tube and its shape is preferably elongated. Additionally, the loop 34 is positioned to preclude occlusion of the passage 28 through sleeve 26.

Turning now to FIG. 3, the gastrostomy device hereof also includes a gastrostomy tube 36. In the form illustrated in FIG. 3, tube 36 includes a pair of concentric tubes comprised of inner and outer tubes 38 and 40, respectively. An inflatable membrane or balloon 42 is provided between end sections of the outer tube 40 whereby air or water received through one branch 44 of a Y-connection at one end of the tube 36 for passage between the inner and outer tubes 38 and 40 may inflate and deflate balloon 42. The other branch 46 of tube 36 is for purposes of supplying food along the inside of inner tube 38 for egress into the stomach through openings 48.

Figure 4B:
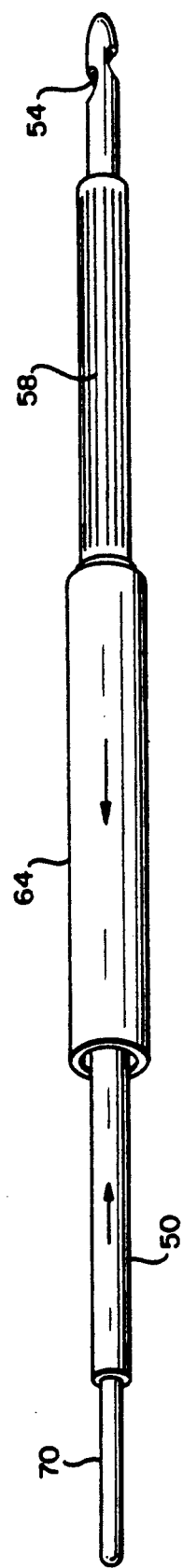
FIG. 4B is a side elevational view of the gastrostomy tube illustrated in FIG. 4A with the retrieval tube applied and the basket in a radially contracted position.

Referring now to FIGS. 4A and 4B, there is illustrated another form of gastrostomy tube which includes an elongated tube 50 having a central passageway 52 for supplying food to the stomach through openings 54 at the opposite end of tube 50. Adjacent the inner end of tube 50, there is provided a basket-type retention device 56, including a plurality of elongated flexible or deformable, but relatively stiff, ribs 58 circumferentially spaced one from the other. The ribs 58 are secured at one end to a collar 60 fixed to tube 50 and at their opposite end to a collar 62 slidable along the tube 50. It will therefore be readily appreciated that by sliding collar 62 along tube 50, the ribs 58 may be radially expanded or contracted between the positions illustrated in FIGS. 4A and 4B, respectively.

As described hereinafter, a retrieval tube 64 may be used to remove the gastrostomy tube from the ostomy tract. The retrieval tube 64 has, in the form of the invention illustrated in FIGS. 4A and 4B, an internally threaded end 66 for threaded engagement with the external threads 68 on slidable collar 62. Consequently, when the retrieval tube 64 is disposed concentrically about tube 50 and rotated to engage the retrieval tube threads and the collar threads, movement of the retrieval tube 64, for example, in the direction of the arrow illustrated in FIG. 4B, radially contracts or flattens out the ribs 58 against the sides of tube 50. Alternatively, a stiff retraction tube 70 may be inserted into the tube 50 to displace tube 50 relative to the retrieval tube 64 whereby the tube 50 is displaced relative to collar 62. In this manner, the ribs 58 may likewise be radially contracted and flattened against the sides of tube 50.

In FIG. 6, there is illustrated a further form of connection between a retrieval tube 50a and the basket retention device 56. In this form, the end of the retrieval tube 64a is provided with a plurality of circumferentially spaced spring fingers 72. Spring fingers 72 cooperate with a cam surface in the form of a tapered collar fixed on tube 50a so that, upon insertion of retrieval tube 64a over tube 50a, spring fingers 72 will then spring back to radially expand and lock behind the cam follower 74. Thus, relative movement between tube 50a and retrieval tube 64a enables the contracting movement of the ribs to flatten out against the side of the gastrostomy tube.

The sleeve, either one or both of the gastrostomy tubes described, as well as other apparatus to be described necessary to the procedure, may form part of a kit.

Referring now to FIGS. 7A-7F, an example of a percutaneous endoscopic gastrostomy procedure according to the present invention will now be described. With the patient prepared as previously described, the endoscopic tube E is passed through the mouth and esophagus of the patient into the stomach. After inspection and air instillation through the endoscope to achieve gastric distension, the endoscope light is used to illuminate the stomach beneath the abdominal wall. The area of maximum trans-illumination is identified as the site for the incision and placement of the gastrostomy tube. After application of local anesthetic, the incision is made. A needle 80, with an internal stylette, is passed through the incision into the stomach under endoscopic observation. After removal of the stylette, a flexible guide wire G is passed through the needle into the stomach and grasped by the endoscopic snare 82. The endoscope E with the guide wire G attached, is then withdrawn from the stomach through the esophagus and out the patient's mouth, drawing with it the end of the guide wire G.

Figure 7A:
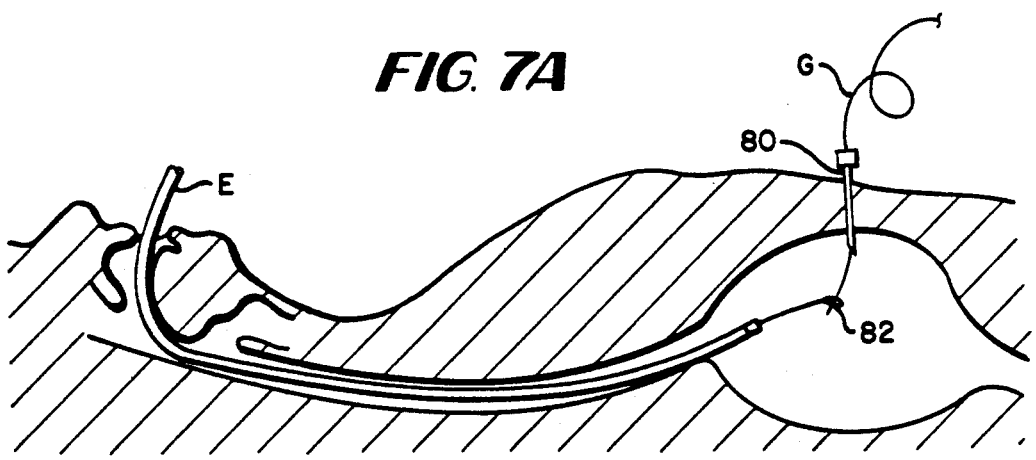
FIGS. 7A–7F are schematic fragmentary cross-sectional views of the upper torso of an individual illustrating a technique for insertion of the gastrostomy tube according to the present invention.
Figure 7B:
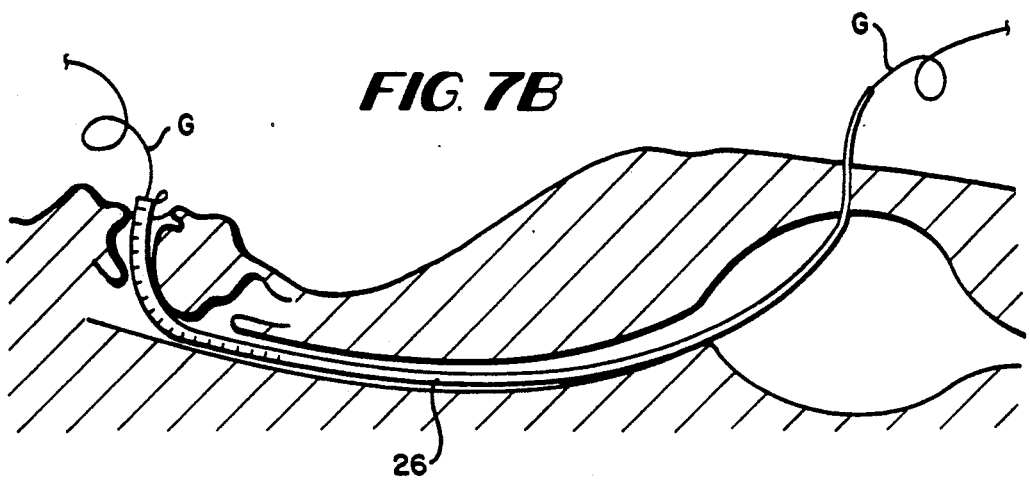
Figure 7C:
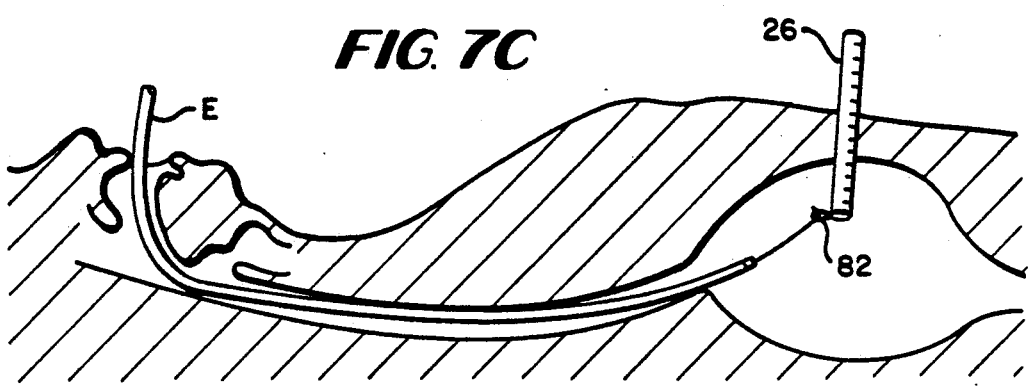
Figure 7D:
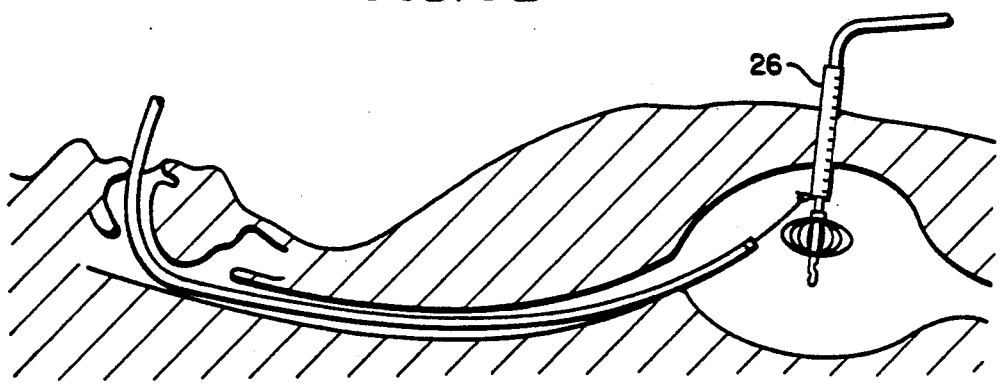

The sleeve is loaded onto the guide wire, tapered end first and, as illustrated in FIG. 7B, advanced over the guide wire through the mouth and esophagus, into the stomach and out through the abdominal wall. The tapered tip of the sleeve is grasped and the sleeve is pulled through the incision to dilate the tract. The endoscope E is reinserted and, under observation, sleeve 26 is withdrawn until only a few centimeters of the end of the sleeve remains within the stomach, as illustrated in FIG. 7C. The graduations 32 on the sleeve facilitate positioning the end of the sleeve within the stomach. Additionally, the retention loop on the intra-gastric portion of the sleeve is grasped by the endoscopic snare to secure and stabilize the sleeve during the remaining portion of the procedure. Guide wire G is then withdrawn through the sleeve and the external portion of the sleeve is cut to leave only a short distance, i.e., several centimeters of the sleeve, above the skin.

Figure 7E:
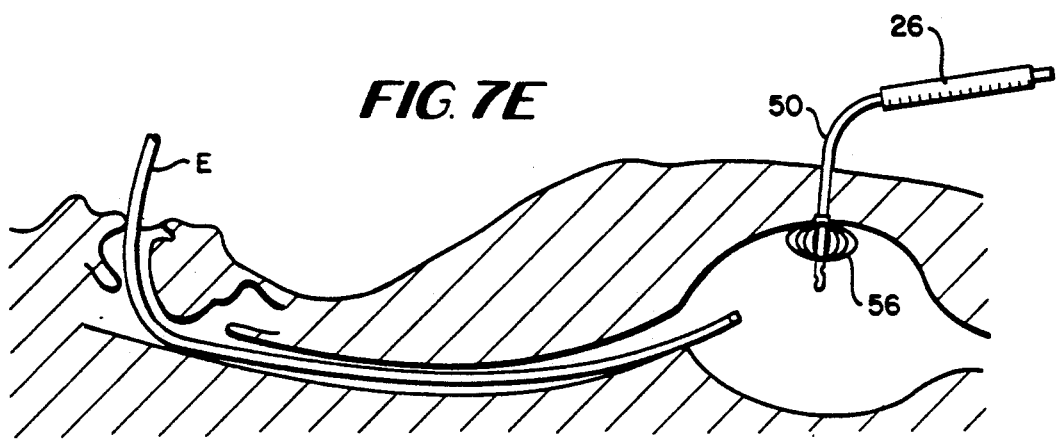
Figure 7F:
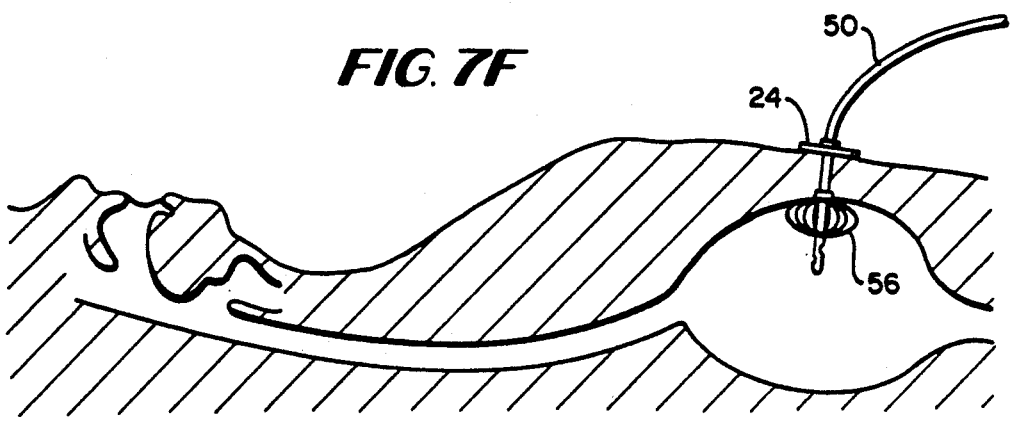
Figure 8A:
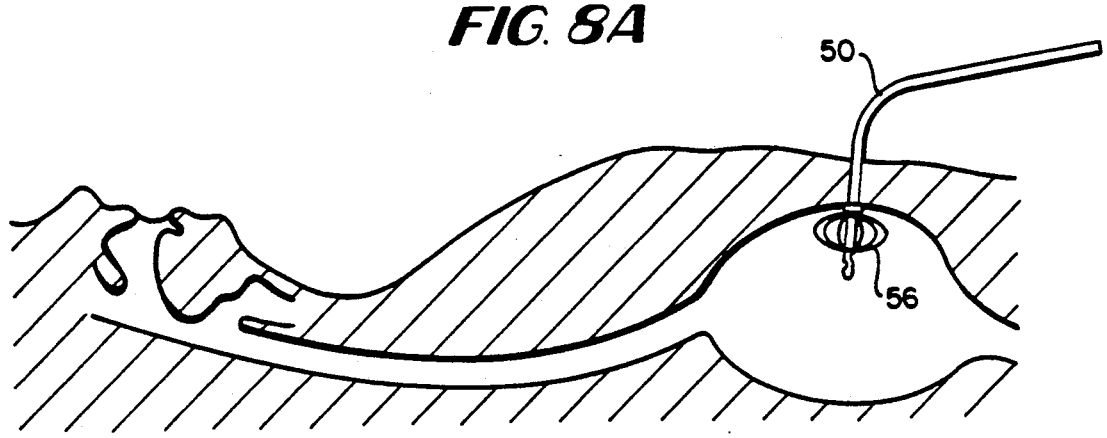
FIGS. 8A–8C illustrate a technique according to the present invention for removal of the gastrostomy tube hereof.
Figure 8B:
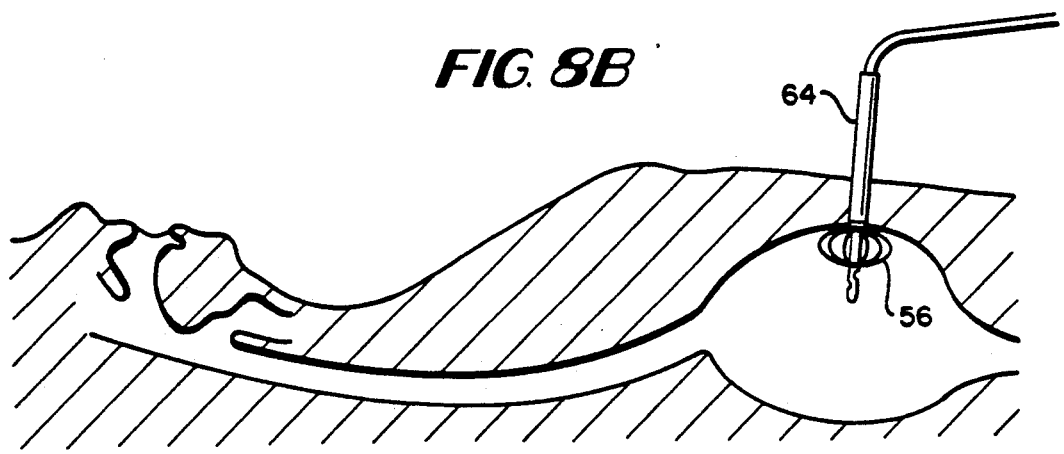
Figure 8C:
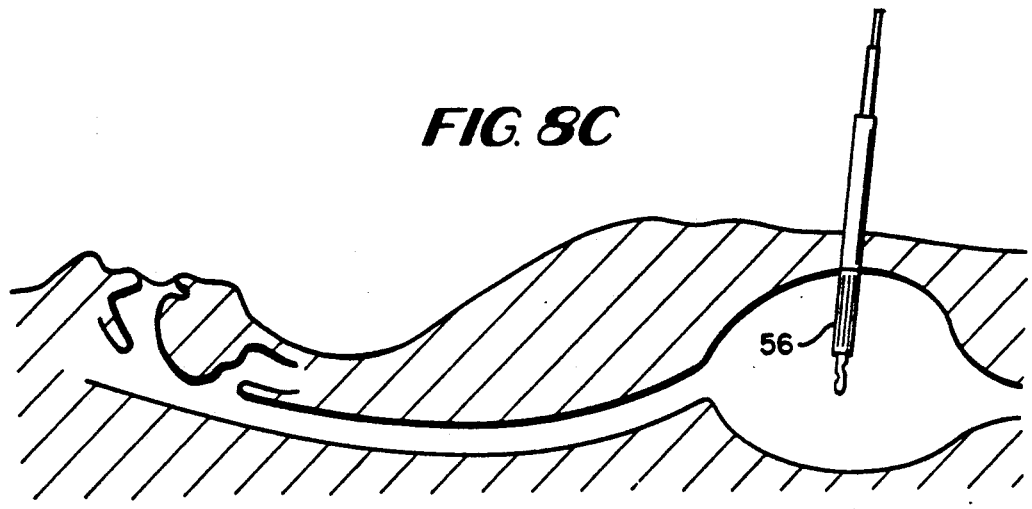

With the retention device on the end of the gastrostomy tube 50 in a deflated or contracted position, the gastrostomy tube 50 is inserted through the shortened sleeve into the stomach under endoscopic observation. Lubrication between the gastrostomy tube 50 and sleeve 26 may be used as necessary or a stiffening wire or rod may be used to facilitate passage of the gastrostomy tube through the shortened sleeve. When the internal retention device has passed beyond the inner end of the sleeve, the retention device is activated, e.g., inflated or expanded, to retain the gastrostomy tube within the stomach. As illustrated in FIG. 7E, the sleeve may then be removed over the gastrostomy tube or it may be cut or peeled away. Alternatively, the sleeve may be left in place for later removal. The gastrostomy tube 50 is then snugged into final position with the internal retention device bearing against the gastric wall. An outer retention device can then be applied and appropriate pressure between the two retention devices is generated to secure the ostomy tract.

A similar procedure is employed when using the gastrostomy tube 36 with the inflatable retention device. Thus, after insertion of the gastrostomy tube 36 through sleeve 26, the branch 44 of gastrostomy tube 36 may be connected to air or water and balloon 42 inflated. With the balloon inflated, the gastrostomy tube 36 can be snugged against the gastric wall and the remaining sleeve portion removed as stated previously.

Another feature of the present invention resides in the capacity to remove the gastrostomy tube and replace it as necessary without the need for endoscopic removal of the internal retention device. Where the basket-type retention device 56 is used on the gastrostomy tube, the retrieval tube 64 may be disposed about the gastrostomy tube and inserted through the ostomy tract. In accordance with the embodiments of the invention hereof illustrated in FIGS. 4 and 6, the retrieval tube 64 may be screw-threaded or snap-fit, with the collar carrying the expansible and retractable ribs 58 of the internal retention device 56. Once that collar is grasped, the gastrostomy tube may be displaced inwardly relative to the retrieval tube to flatten out or radially contract the ribs 58. Once flattened, the retrieval tube and gastrostomy tube may be removed jointly or sequentially. Where the gastrostomy tube uses the balloon retention device, a stopcock, not shown, on the gastrostomy tube may be opened and the balloon deflated whereby the gastrostomy tube and retrieval tube can be removed from the ostomy tract.

The present invention also includes as part of a kit a feeding jejunostomy tube which may be used in lieu of the gastrostomy tube previously described. The jejunostomy tube is identical to the previously described gastrostomy tube, except that the internal portion of the tube below the retention device would be extended or elongated for positioning endoscopically or radiographically in the duodenum. Additionally, the tip of the jejunostomy tube is internally weighted to facilitate passage into the jejunum. The feeding exit openings are located just above the weighted tip of the jejunostomy tube to allow feeding fluid to pass from the tube. The jejunostomy tube may also be provided with a second internal tube, either concentrically or radially spaced from the feeding tube so that the second tube may terminate in openings in the stomach. This allows for simultaneous gastric decompression.

Figure 9A:
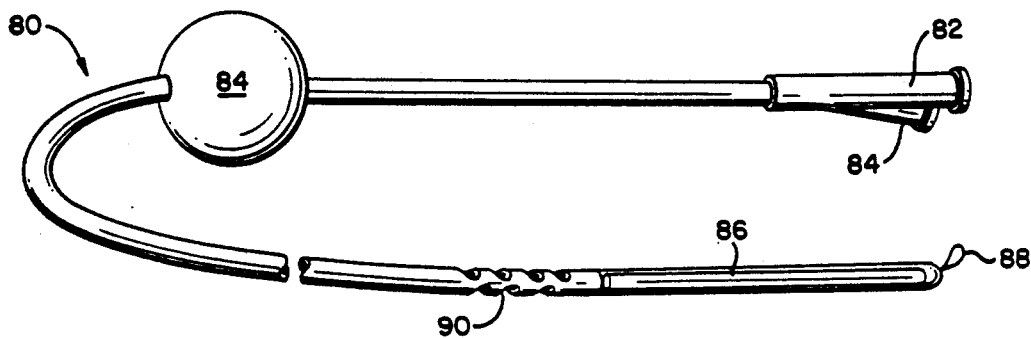
FIGS. 9A, 9B and 9C are perspective views of jejunostomy tubes with FIG. 9A illustrating a balloon retention type, FIG. 9B illustrating a basket retention type and FIG. 9C illustrating a balloon retention device with a double lumen jejunostomy tube for feeding and gastric decompression.

For example, in FIG. 9A, there is illustrated a jejunostomy tube, generally designated 80, having a balloon port 82 for expanding and contracting a balloon 84 located about tube 80 and a feeding port 84. The distal end of the jejunostomy tube 80 is provided with internal weights 86, a thread loop 88 projecting from its distal end, and drain openings 90. This jejunostomy tube is used similarly as described with the gastrostomy tube, except that, upon inflation, the endoscopic snare or forceps is used to grasp the thread loop to advance the distal end of the jejunostomy tube into the small bowel. Upon release, and removal of a stiffening wire, if used, the jejunostomy tube is in position for feeding the small bowel.

Figure 9B:
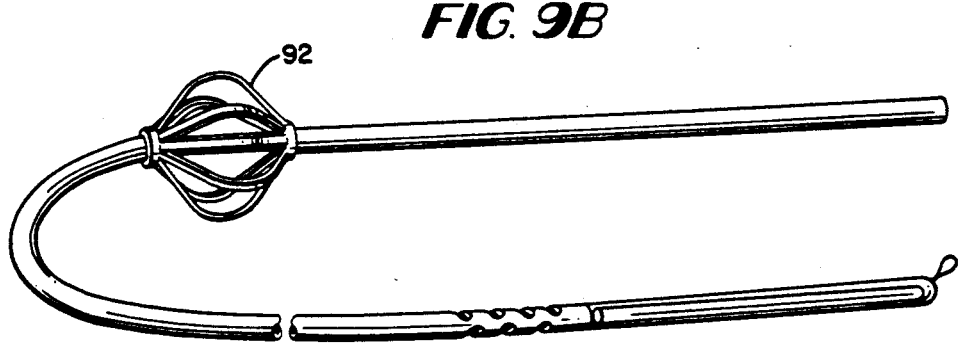

In FIG. 9B, there is illustrated a similar jejunostomy tube, except that in lieu of the balloon retention device illustrated in FIG. 9A, a basket-type retention device 92 is used. In all other respects, the jejunostomy tube of FIG. 9A is used similarly as the jejunostomy tube of FIG. 9B.

Figure 9C:
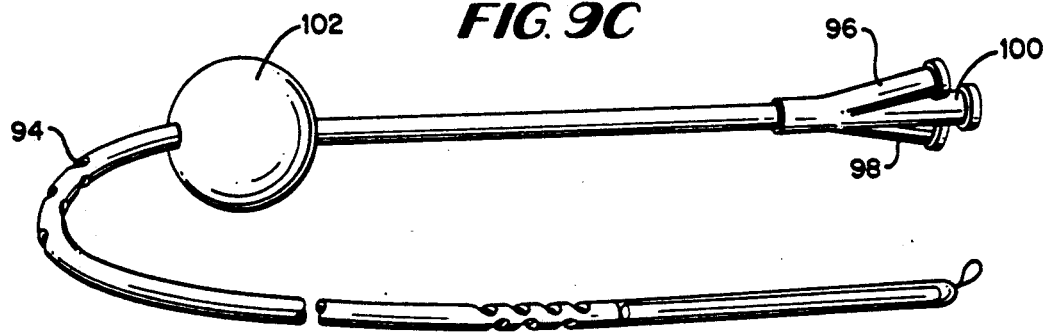

In FIG. 9C, the jejunostomy tube 94 has a double lumen throughout its length in order to permit gastric decompression simultaneously with feeding. To accomplish this, the proximal end has a balloon port 96, a feeding port 98 and a gastric port 100. The feeding port 98 and gastric port 100 extend through the distal end to enable simultaneous decompression and feeding. The balloon port 96, of course, is used to inflate and deflate the balloon 102.

Figure 10:
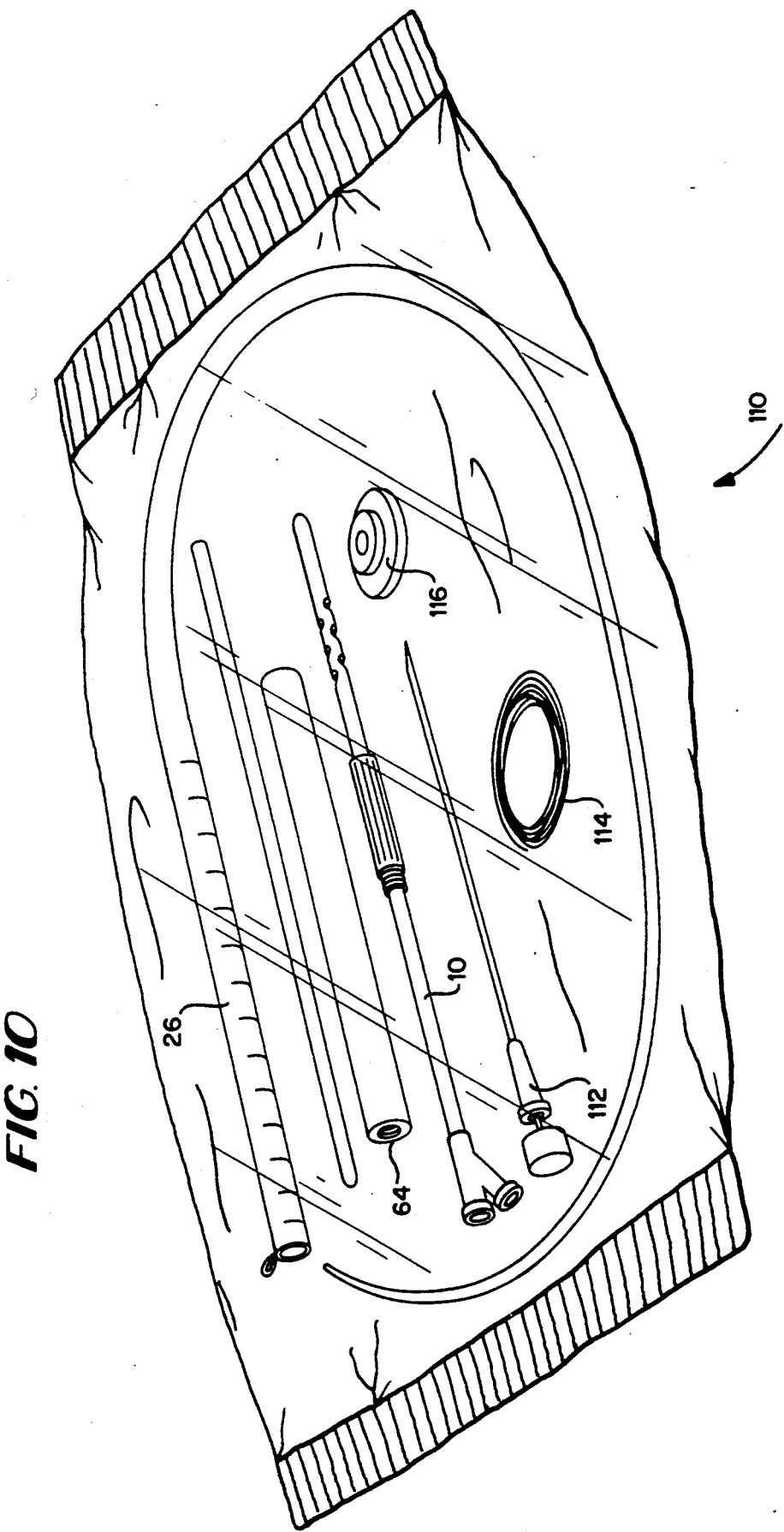
FIG. 10 is a representative example of a gastrostomy tube insertion kit.

In FIG. 10, there is disclosed a gastrostomy tube insertion kit, generally designated 110. The kit includes a sleeve tube 26, a needle cannula 112 with stylette, a guide wire 114, a retrieval tube 64 and stiffening rod (for basket-type retention devices), a gastrostomy tube 10 (basket or balloon type) and an external retention device 116. If desired, one or more of the following devices may also be included within the kit: an inflation syringe (for balloon-type retention devices), a scalpel, local anesthetic, syringe and needle for local anesthetic, gauze, sterile drape, cleansing solution and scissors. To provide a jejunostomy tube insertion kit, the kit would include the essentials of the gastrostomy tube insertion kit, with one or more of the non-essential but desirable elements as described above, but also with a jejunostomy tube substituted for the gastrostomy tube. A replacement gastrostomy tube kit may also be provided containing only a gastrostomy tube and a retrieval tube and stiffener (for basket-type retention devices). Additionally, an inflation syringe (for balloon-type retention devices) may be included in the kit in lieu of the stiffener. A replacement jejunostomy tube kit may also be provided similarly as the replacement gastrostomy tube kit, except for the substitution of the jejunostomy tube for the gastrostomy tube.

The kit itself may comprise flexible plastic packaging whereby the components of the kit may be maintained sterile. Alternatively, the kit may be provided in a more rigid form, i.e., a rigid box formed, for example, of plastic material.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method for percutaneous endoscopic gastrostomy using a guide wire, a sleeve having a tapered end and a gastrostomy tube having a retention device adjacent one end, comprising the steps of:
    (a) passing an endoscope through a patient's mouth and esophagus and into the patient's stomach;
    (b) introducing the guide wire through the patient's abdominal and gastric walls and into the patient's stomach;
    (c) grasping a portion of the guide wire within the stomach;
    (d) pulling the endoscope and guide wire from the stomach out the patient's mouth;
    (e) passing the sleeve, tapered end first, over the wire through the patient's mouth, esophagus and stomach and out through the abdominal and gastric walls, leaving terminal portions of the sleeve on opposite sides of the abdominal and gastric walls;
    (f) withdrawing the guide wire from the sleeve;
    (g) inserting the gastrostomy tube through the sleeve to locate the end thereof carrying the retention device within the stomach; and
    (h) activating the retention device to retain the gastrostomy tube within the stomach.

2. The method according to claim 1 including the step of withdrawing the sleeve from about the gastrostomy tube.

3. The method according to claim 1 wherein the retention device adjacent the end of the gastrostomy tube includes an expansion element, the step of activating the retention device, including laterally expanding the retention device after insertion of the gastrostomy tube through the sleeve to retain the gastrostomy tube in the stomach.

4. The method according to claim 3 wherein the retention device includes an inflatable element and the step of activating the retention device includes inflating the inflatable element for lateral expansion within the stomach.

5. The method according to claim 1 including the steps of withdrawing the sleeve, leaving the end of the gastrostomy sleeve retained in the stomach and applying a retention device about the gastrostomy tube externally of the abdominal wall to clamp the gastrostomy tube to the abdominal and gastric walls.

6. The method according to claim 1 including clamping the gastrostomy tube to the abdominal and gastric walls using the retention device at one end thereof in the stomach to preclude withdrawal of the gastrostomy tube from the stomach through the abdominal and gastric walls.

7. Apparatus for performing percutaneous endoscopic gastrostomy comprising:
    an elongated flexible guide wire having a length sufficient to extend from a location outside the abdominal wall of a patient through the patient's stomach and esophagus and out the patient's mouth;
    an elongated sleeve having a tapered end portion and an internal diameter sized to enable slidable movement thereof along said guide wire, said sleeve having a length sufficient to extend from a location outside the abdominal wall of a patient through the patient's stomach and esophagus and out the patient's mouth; and
    a gastrostomy tube for reception within said sleeve and having a retention device adjacent an end portion thereof for retaining the gastrostomy tube within the patient's stomach in position for feeding.

8. Apparatus according to claim 7 wherein said sleeve has graduations along an end thereof opposite the tapered end portion.

9. Apparatus according to claim 7 wherein said sleeve is tapered a distance at least about substantially one-half its length.

10. Apparatus according to claim 7 wherein said sleeve has a catch adjacent the end thereof remote from the tapered end portion.

11. Apparatus according to claim 10 wherein said catch comprises a loop.

12. Apparatus according to claim 7 wherein said sleeve is tapered a distance at least about substantially one-half its length, said sleeve having a catch adjacent the end thereof remote from the tapered end portion.

13. Apparatus according to claim 8 wherein said sleeve has a catch adjacent the end thereof remote from the tapered end portion.

14. Apparatus according to claim 7 wherein said retention device includes an inflatable member and means carried by said gastrostomy tube at a location remote from said inflatable member for inflating said member and laterally enlarge said gastrostomy tube adjacent said end portion thereof.

15. Apparatus according to claim 7 wherein said retention device includes a member movable between a first position wherein said member has a diameter substantially corresponding to the diameter of said gastrostomy adjacent said end portion thereof and a second position wherein said member extends laterally outwardly of said gastrostomy tube thereby to preclude passage of the gastrostomy tube through an opening corresponding to the diameter thereof.

16. Apparatus according to claim 15 wherein said retention member includes an element slidable along said gastrostomy tube between first and second locations along said gastrostomy tube corresponding to said first and second positions of said member, respectively, and means carried by said gastrostomy tube engageable with said element and movable from a location along said gastrostomy tube remote from said member for moving said element between said first and second locations.

17. Apparatus according to claim 16 wherein said element includes a connecting tube for slidable movement along said gastrostomy tube for engaging said element.

18. Apparatus according to claim 17 wherein said element and said connecting tube have cooperable screw threads for connecting said element and said connecting tube one to the other.

19. Apparatus according to claim 17 wherein said element and said connecting tube have cooperable hook and abutment portions for releasably coupling said element and said connecting tube one to the other.

20. A percutaneous endoscopic kit comprising:
a container;
a needle cannula with stylette in said container;
an elongated flexible guide wire in said container, said wire having a length sufficient to extend from a location outside the abdominal wall of a patient through the patient's stomach and esophagus and out the patient's mouth;
an elongated sleeve in said container and having a tapered end portion and an internal diameter sized to enable slidable movement thereof along said guide wire, said sleeve having a length sufficient to extend from a location outside the abdominal wall of a patient through the patient's stomach and esophagus and out the patient's mouth;
one of a gastrostomy tube or jejunostomy tube in said container for reception within said sleeve; and
a retention device in said container for location adjacent an end portion of said one tube for retaining said one tube in position for feeding.

21. A kit according to claim 20 including one or more of a scalpel, a local anesthetic, a syringe and needle for applying local anesthetic, gauze, a sterile drape, a cleansing solution and scissors.

* * * * *